(12) United States Patent
Morishige et al.

(10) Patent No.: US 8,748,157 B2
(45) Date of Patent: Jun. 10, 2014

(54) METHOD FOR PRODUCING HYDROXYCARBOXYLIC ACID BY REGENERATING COENZYME

(75) Inventors: Takashi Morishige, Mobara (JP); Mitsufumi Wada, Mobara (JP); Hitoshi Takahashi, Chiba (JP); Daisuke Mochizuki, Mobara (JP); Junko Tokuda, Chiba (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 0 days.

(21) Appl. No.: 12/299,679

(22) PCT Filed: Apr. 27, 2007

(86) PCT No.: PCT/JP2007/000471
§ 371 (c)(1),
(2), (4) Date: Nov. 5, 2008

(87) PCT Pub. No.: WO2007/129466
PCT Pub. Date: Nov. 15, 2007

(65) Prior Publication Data
US 2009/0305368 A1 Dec. 10, 2009

(30) Foreign Application Priority Data
May 9, 2006 (JP) .................................. 2006-129986

(51) Int. Cl.
*C12N 1/20* (2006.01)
*C12N 9/04* (2006.01)
*C12N 15/00* (2006.01)
*C12P 21/06* (2006.01)
*C12P 7/42* (2006.01)
*C07H 21/04* (2006.01)

(52) U.S. Cl.
USPC ............. 435/252.33; 435/69.1; 435/146; 435/190; 435/320.1; 536/23.2

(58) Field of Classification Search
None
See application file for complete search history.

(56) References Cited

U.S. PATENT DOCUMENTS

| 2003/0032153 A1 | 2/2003 | Yamamoto et al. |
| 2003/0171544 A1 | 9/2003 | Riermeir et al. |

FOREIGN PATENT DOCUMENTS

| EP | 1 170 376 A1 | 1/2002 |
| EP | 1 748 076 A1 | 1/2007 |
| JP | 10-174593 A | 6/1998 |
| JP | 10-174594 A | 6/1998 |
| JP | 2002-345479 A | 12/2002 |
| JP | 2004-159587 A | 6/2004 |
| JP | 2005-218349 A | 8/2005 |
| WO | WO 2005/106005 A1 | 11/2005 |

OTHER PUBLICATIONS

Whisstock et al. Quaterly Reviews of Biophysics, 2003, "Prediction of protein function from protein sequence and structure", 36(3): 307-340.*
Chica et al. Semi-rational approaches to engineering enzyme activity: combining the benefits of directed evolution and rational design, Curr Opin Biotechnol. Aug. 2005;16(4):378-84. Review.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Nantapong et al. Effect of NADH dehydrogenase-disruption and over-expression on respiration-related metabolism in Corynebacterium glutamicum KY9714, Appl Microbiol Biotechnol 2004, 66: 187-193.*
Form PCT/ISA/210 (International Search Report) dated Jul. 17, 2007.
Zhe Lu et al., "Evolution of an *Escherichia coli* Protein With Increased Resistance to Oxidative Stress", The Journal of Biological Chemistry, Apr. 3, 1998, vol. 273, No. 14, pp. 8308-8316, The American Society for Biochemistry and Molecular Biology, Inc.
Nadia Raffaelli et al., "The *Escherichia coli* NadR Regulator Is Endowed With Nicotinamide Mononucleotide Adenylyltransferase Activity", Journal of Bacteriology, Sep. 1999, vol. 181, No. 17, pp. 5509-5511, American Society for Microbiology.
Marcel G. Wubbolts et al., "Variation of Cofactor Levels in *Escherichia coli*", The Journal of Biological Chemistry, Oct. 15, 1990, vol. 265, No. 29, pp. 17665-17672, The American Society for Biochemistry and Molecular Biology, Inc.
Laura Baldoma et al., "Involvement of Lactaldehyde Dehydrogenase in Several Metabolic Pathways of *Escherichia coli* K12", The Journal of Biological Chemistry, Oct. 15, 1987, vol. 262, No. 29, pp. 13991-13996, The American Society for Biochemistry and Molecular Biology, Inc.
Susana J. Berrios-Rivera et al., "The Effect of Naprtase Overexpression on the Total Levels of NAD, The NADH/NAD+ Ratio, and The Distribution of Metabolites in *Escherichia coli*", Metabolic Engineering, 2002, vol. 4, pp. 238-247, Elsevier Science, USA.
Anna V. Gerasimova et al., "Evolution of the NADR Regulon in Enterobacteriaceae", Bioinformatics and Computational Biology, Aug. 2005, vol. 3, No. 4, pp. 1007-1019.
Michihiko Kataoka et al., "Glycolic Acid Production Using Ethylene Glycol-Oxidizing Microorganisms", Biosci. Biotechnol. Biochem., 2001, vol. 65, No. 10, pp. 2265-2270.
Julianne H. Grose et al., "Regulation of NAD Synthesis by the Trifunctional NadR Protein of *Salmonella Enterica*", Journal of Bacteriology, Apr. 2005, vol. 187, No. 8, pp. 2774-2782, American Society for Microbiology.
Official Action issued on Jun. 24, 2011 by the Chinese Patent Office in corresponding Chinese Patent Application No. 200780016258.9.
Extended Search Report from European Patent Office issued in corresponding European Patent Application No. 07737127.6 dated Nov. 8, 2011.
Berrios-Rivera et al., "The Effect of NAPRTase Overexpression on the Total Levels of NAD, the NADH/HAD+Ratio, and the Distribution of Metabolites in *Escherichia coli*," Metabolic Engineering, Jan. 1, 2002, vol. 4, No. 3, pp. 238-247, Academic Press, US, XP003016934, ISSN: 1096-7176.

* cited by examiner

*Primary Examiner* — Iqbal H Chowdhury
(74) *Attorney, Agent, or Firm* — Buchanan Ingersoll & Rooney PC (57) ABSTRACT

Hydroxycarboxylic acids are produced by using a microorganism that is improved in ability to regenerate oxidized-type nicotinamide adenine dinucleotide by being provided with an enhanced NADH dehydrogenase function by introducing a gene encoding NADH dehydrogenase into a microorganism.

3 Claims, 1 Drawing Sheet

METHOD FOR PRODUCING HYDROXYCARBOXYLIC ACID BY REGENERATING COENZYME

TECHNICAL FIELD

The present invention relates to a microorganism which produces hydroxycarboxylic acids including glycolic acid and a method for producing hydroxycarboxylic acids including glycolic acid by using the microorganism.

BACKGROUND ART

Since hydroxycarboxylic acids are useful as a raw material for polymers or an intermediate for medicines, a method for effectively producing hydroxycarboxylic acids have been demanded.

As an example, glycolic acid (α-hydroxyacetic acid) can be mentioned. Glycolic acid has been used as a raw material for cleaning agents or cosmetics, but has recently received attention as a raw material for polyglycolic acid which is useful as a gas barrier polymer or a medical polymer. The reason why glycolic acid has received attention as a gas barrier material is that a layer of polyglycolic acid has high oxygen barrier property and performance as a material for packing food or carbonated beverage which can easily spoil in the presence of oxygen.

Glycolic acid of a chemically synthesized product which is currently commercially available contains quite a few impurities, which is a problem when used as a raw material for polymers in view of purity. This is because these impurities inhibit a dehydrating condensation reaction of glycolic acid, and also methoxy acetate which is one of those impurities is a compound suspicious of carcinogenic potential, thus being desirable not to be included in a packing material for food or beverage. It is technically possible to remove impurities by purification, but such the purified products are high in cost and thus are not practical as a raw material for packing at low cost.

In order to avoid the aforementioned problems given in glycolic acid of chemically synthesized products, a production of glycolic acid according to a biomethod employing ethylene glycol as a raw material has been attempted. In Patent Document 1 and Patent Document 2, there has been disclosed a method for producing glycolic acid by a microorganism, which includes culturing yeast belonging to genus *Pichia*, genus *Rhodotorula*, genus *Sporobolomyces*, genus *Kluyveromyces* or genus *Torulopsis*, a strain belonging to genus *Nocardia*, a strain belonging to genus *Rhodococcus*, or an *Escherichia coli* B strain in a culturing medium containing ethylene glycol and separating and collecting glycolic acid from the culturing broth. Among the methods for producing glycolic acid as described in Examples of Patent Document 1 and Patent Document 2, a method employing *Pichia naganishii* gives the highest accumulation concentration of glycolic acid, and 35.3 g/L of glycolic acid is obtained by a reaction for 30 hours. In regard to the production of glycolic acid with the use of *Pichia naganishii*, it has been reported in Non-Patent Document 1 that 105 g/L of glycolic acid can be obtained by a reaction for 120 hours with further improved reaction conditions.

In Patent Document 3, it has been described that it is possible to produce hydroxycarboxylic acids including glycolic acid from a raw material like aliphatic polyhydric alcohols having a hydroxyl group at the end such as ethylene glycol, by using a microorganism in which a gene encoding lactaldehyde reductase and a gene encoding lactaldehyde dehydrogenase are introduced in the form of plasmid so as to impart or enhance an activity of those enzymes, as well as described that an ability to produce glycolic acid is improved by disrupting a gene encoding glycolate oxidase contained in a microorganism so as to inactivate an activity of the enzyme.

In a reaction for producing hydroxycarboxylic acids including glycolic acid by the above-mentioned conventional methods, an amount of microbial cell required for the reaction is large, which thereby causes problems such as an increase in the production cost, contamination by impurities derived from the microbial cells, and requiring so much work and cost for disposing the microbial cells after the production of hydroxycarboxylic acids.

In a method for producing ketone from alcohol using an oxidase, a technique as described below that oxidized-type nicotinamide adenine dinucleotide (hereinafter, may be referred to as NAD) needed for a reaction is regenerated from reduced-type nicotinamide adenine dinucleotide (hereinafter, may be referred to as NADH) produced in accompany with the reaction has been employed. That is, there are a method of combining two reactions of an oxidation reaction to produce a purposed ketone and a reduction reaction of ketone to regenerate NAD are combined, a technique combined with a reduction reaction of oxoglutaric acid by glutamic acid dehydrogenase, and the like.

In the above technique to regenerate NAD, there may been mentioned problems that it is needed to add a reaction substrate to regenerate NAD into the reaction system and that by-products from the reaction to regenerate NAD are accumulated in the reaction system.

In the production of ketone from alcohol, there has been disclosed a method to make up for the above problems, in which NADH dehydrogenase is used for regenerating NAD by a reduction of molecular-form oxygen via respiration chain of a microorganism to produce water (Patent Document 4), but actual examples of microorganisms having enhanced activity of the enzyme has not been reported.

[Patent Document 1] Japanese Patent Laid-open No. H10-174593
[Patent Document 2] Japanese Patent Laid-open No. H10-174594
[Patent Document 3] International Publication Pamphlet No. WO 2005/106005
[Patent Document 4] Japanese Patent Laid-open No. 2005-218349
[Non-Patent Document 1] Biosci. Biotechnol. Biochem., Vol. 65(10), pp. 2265-2270, (2001)

DISCLOSURE OF THE INVENTION

A chemical synthesis method is not good enough from the viewpoint of purity of hydroxycarboxylic acids to be obtained, and a conventional biomethod gives a problem in strain disposal as a large amount of microbial cell is used in the production reaction.

It is an object of the present invention to provide an industrially advantageous method for producing hydroxycarboxylic acids, by which hydroxycarboxylic acids can be efficiently produced using a small amount of microbial cell, and a microorganism suitable for the production method.

From the results of studies to solve the above objects, the present inventors have found that hydroxycarboxylic acids can be efficiently produced by using a microorganism in which an ability to regenerate oxidized-type nicotinamide adenine dinucleotide is enhanced, in a method for producing a hydroxycarboxylic acid from aliphatic polyhydric alcohol having a hydroxyl group at the end by using a microorganism.

That is, the present invention is as described by [1] to [9] herein below.

[1] A method for producing a hydroxycarboxylic acid from an aliphatic polyhydric alcohol having a hydroxyl group at the end by using a microorganism, where the method includes using the microorganism which has an enhanced activity of NADH dehydrogenase.

[2] The production method as set forth in [1], wherein the microorganism has an enhanced activity of at least one enzyme of lactaldehyde reductase and lactaldehyde dehydrogenase.

[3] The production method as set forth in [1], wherein the microorganism has an inactivated or lowered activity of glycolate oxidase than the activity of existing microorganism.

[4] The production method as set forth in [2], wherein the microorganism has an inactivated or lowered activity of glycolate oxidase than the activity of existing microorganism.

[5] The production method as set forth in any one of [1] to [4], wherein the aliphatic polyhydric alcohol having a hydroxyl group at the end is ethylene glycol and the hydroxycarboxylic acid is glycolic acid.

[6] A microorganism, which has an enhanced activity of at least one enzyme of lactaldehyde reductase and lactaldehyde dehydrogenase, and an enhanced activity of NADH dehydrogenase.

[7] The microorganism as set forth in [6], wherein the activity of glycolate oxidase is inactivated or lowered than the activity of existing microorganism.

[8] The production method as set forth in any one of [1] to [5], wherein the microorganism is *Escherichia coli*.

[9] The microorganism as set forth in [6] or [7], which is *Escherichia coli*.

According to the present invention, hydroxycarboxylic acids can be efficiently produced using a small amount of microbial cell.

BRIEF DESCRIPTION OF THE DRAWINGS

The above objects and other objects, features and advantages will be clearer with reference to the best modes for carrying out the invention and the figures described hereinafter.

BEST MODE FOR CARRYING OUT THE INVENTION

The present invention will be described in more detail below.

The present embodiment relates to a method for producing a hydroxycarboxylic acid. This method is a method for producing a hydroxycarboxylic acid from an aliphatic polyhydric alcohol having a hydroxyl group at the end by using a microorganism, which comprises using a microorganism with enhanced activity of NADH dehydrogenase.

The microorganism may be any of those capable of having an ability to produce a hydroxycarboxylic acid from an aliphatic polyhydric alcohol having a hydroxyl group at the end by using any means, regardless of whether or not it inherently has an ability to produce a hydroxycarboxylic acid from an aliphatic polyhydric alcohol having a hydroxyl group at the end. As such a microorganism, there may be exemplified by preferably bacteria, actinomycetes, yeasts and molds for which hosts vector systems have been developed, such as genus *Escherichia*, genus *Bacillus*, genus *Pseudomonas*, genus *Serratia*, genus *Brevibacterium*, genus *Corynebacterium*, genus *Streptococcus*, genus *Lactobacillus*, genus *Rhodococcus*, genus *Streptomyces*, genus *Saccharomyces*, genus *Kluyveromyces*, genus *Schizosaccharomyces*, genus *Zygosaccharomyces*, genus *Yarrowia*, genus *Trichosporon*, genus *Rhodosporidium*, genus *Pichia*, genus *Candida*, genus *Neurospora*, genus *Aspergillus*, genus *Cephalosporium*, genus *Trichoderma*, and more preferably *Escherichia coli*.

Further, the aliphatic polyhydric alcohol is not particularly limited in its structure if it is an aliphatic compound having a hydroxyl group having at the end of a carbon chain and having at least two hydroxyl groups in the molecule, but examples of such a compound may include ethylene glycol, diethylene glycol, glycerol, 1,3-propanediol, 1,2-butanediol, 1,3-butanediol, 1,4-butanediol, 1,2,4-butanetriol and the like.

Further, the hydroxycarboxylic acid refers to a compound in which one of the end carbons having hydroxyl groups in the molecule of the aliphatic polyhydric alcohol having a hydroxyl group at the end is oxidized to be a carboxylic acid. Examples of such a compound may include glycolic acid, hydroxyethoxyacetic acid, glyceric acid, 3-hydroxypropionic acid, 2-hydroxybutanoic acid, 3-hydroxy hydroxybutanoic acid, 4-hydroxy hydroxybutanoic acid, 2,4-dihydroxy hydroxybutanoic acid and the like. In the present embodiment, the nicotinamide adenine dinucleotide indicates either of oxidized-type or reduced-type if not specified.

In the present embodiment, ethylene glycol may be properly used as the aliphatic polyhydric alcohol having a hydroxyl group at the end. Further, glycolic acid may be properly used as the hydroxycarboxylic acid.

Here, the NADH dehydrogenase is classified into the enzyme number 1.6.5.3, 1.6.99.3 or 1.6.99.5, based on the report of the enzyme committee of International Union of Biochemistry (I.U.B.), and refers to a generic name of an enzyme which reversibly catalyzes a reaction to generate NAD from NADH using quinones such as ubiquinone, dimethylmenaquinone, menaquinone and the like as an electron acceptor. Preferred is the NADH dehydrogenase which is classified into the enzyme number 1.6.99.3, based on the report of the enzyme committee of International Union of Biochemistry (I.U.B.). In *Escherichia coli*, the NADH dehydrogenase encoded at the ndh gene which is reported by GenBank accession number V00306 may be exemplified.

Enhancing activity of NADH dehydrogenase preferably means that the activity is enhanced by 2 times or more compared to that before the enhancement. Microorganisms in which the enzyme activity is enhanced can be produced, for example, by using a method of introducing a gene encoding the enzyme into a wild type microorganism (or a microorganism prior to recombination) according to a gene recombination technique, a method of introducing a mutation to a promoter of a gene encoding the enzyme in the genome, and the like. As a method for introducing the gene into the wild type microorganism (or a microorganism prior to recombination), there may be mentioned a method of introducing the gene into the microorganism in the form of plasmid. Preparation of the genome DNA used for introduction of a gene into a microorganism, preparation of plasmid, cleavage and ligation of DNA, transformation, PCR (Polymerase Chain Reaction), design and synthesis of oligonucleotide used as a primer and the like can be carried out according to usual methods well known to the skilled person in the art. These methods have been disclosed in Sambrook, J., et. al., "Molecular Cloning A Laboratory Manual, Second Edition", Cold Spring Harbor Laboratory Press, (1989), and the like.

Further, a microorganism related to the present embodiment has enhanced activity of at least one enzyme of lactaldehyde reductase and lactaldehyde dehydrogenase.

Here, the lactaldehyde reductase is classified into the enzyme number 1.1.1.77, based on the report of the enzyme committee of I.U.B., and refers to a generic name of an enzyme that reversibly catalyzes a reaction to produce lactaldehyde from 1,2-propanediol in the presence of NAD, which is a coenzyme.

In addition, the lactaldehyde dehydrogenase is classified into the enzyme number 1.2.1.22, based on the report of the enzyme committee of I.U.B. and refers to a generic name of an enzyme that catalyzes a reaction to produce lactic acid from lactaldehyde in the presence of NAD, which is a coenzyme, and also the lactaldehyde dehydrogenase is classified into the enzyme number 1.2.1.21, based on the report of the enzyme committee of I.U.B. and refers to a generic name of an enzyme glycolaldehyde dehydrogenase that catalyzes a reaction to produce glycolic acid from glycolaldehyde in the presence of NAD, which is a coenzyme. This is because there has been reported in the previous literature using *Escherichia coli* that lactaldehyde dehydrogenase and glycolaldehyde dehydrogenase are the same enzyme (Caballero, E., et al., J. Biol. Chem., Vol. 258, pp. 7788-7792 (1983).

Further, being enhanced in activity of at least one enzyme of lactaldehyde reductase and lactaldehyde dehydrogenase means that, for example, in *Escherichia coli*, activity of at least one enzyme of these enzymes is preferably enhanced by 20 times or more, and more preferably by 100 times or more, in comparison with a wild strain (or a microorganism prior to recombination).

These microorganisms which are enhanced in activity of the enzyme can be produced, for example, by using a method of introducing a gene encoding the enzyme into a wild type microorganism (or a microorganism before recombination) with a gene recombination technique, a method of introducing a mutation to a promoter of a gene encoding the enzyme in the genome, or the like. As a method for introducing the gene into the wild type microorganism (or a microorganism prior to recombination), a method for introducing the gene into the microorganism in the form of plasmid can be mentioned. Preparation of the genome DNA used for introduction of a gene into a microorganism, preparation of plasmid, cleavage and ligation of DNA, transformation, PCR (Polymerase Chain Reaction), design and synthesis of oligonucleotide used as a primer and the like can be carried out according to a usual method well known to the skilled person in the art. These methods have been disclosed in the above-mentioned literature by Sambrook, J., et al.

For example, *Escherichia coli* that is enhanced in the enzyme activity of lactaldehyde reductase and lactaldehyde dehydrogenase can be prepared as described below.

The base sequence of the gene (hereinafter may be abbreviated as fucO) of lactaldehyde reductase of *Escherichia coli* has been already reported (GenBank accession number M31059). Further, the base sequence of the gene (hereinafter may be abbreviated as aldA) of lactaldehyde dehydrogenase of *Escherichia coli* has been also already reported (GenBank accession number M64541).

In order to acquire fucO, oligonucleotide to be a primer is used for a PCR amplification using the genome DNA of *Escherichia coli* as a template, and the obtained DNA fragment was digested with a restriction enzyme to obtain a fucO fragment.

Further, in order to acquire aldA, oligonucleotide to be a primer is used for a PCR amplification using the genome DNA of *Escherichia coli* as a template, and the obtained DNA fragment was digested with a restriction enzyme to obtain an aldA fragment.

In addition, in order to acquire a glyceraldehyde 3-phosphate dehydrogenase (GAPDH) promoter, oligonucleotide to be a primer is used for a PCR amplification using the genome DNA of *Escherichia coli* as a template, and the obtained DNA fragment was digested with a restriction enzyme to obtain a DNA fragment encoding a GAPDH promoter.

The above 3 DNA fragments are ligated with a fragment obtained by digesting a plasmid with restriction enzymes and then transformed into *Escherichia coli* to obtain a transformant which grows on an LB agar plate. The obtained colony is cultured in an LB liquid culture medium and the plasmid is recovered from the obtained microbial cells. By introducing the plasmid into any host *Escherichia coli*, *Escherichia coli* which is enhanced in enzyme activity of lactaldehyde reductase and lactaldehyde dehydrogenase can be prepared.

In the microorganisms related to the present embodiment, activity of glycolate oxidase is inactivated or lowered as compared to that of existing microorganisms.

Here, the glycolate oxidase is classified into the enzyme number 1.1.3.15, based on the report of the enzyme committee of I.U.B. and refers to a generic name of an enzyme that reversibly catalyzes a reaction to produce glyoxylic acid from glycolic acid.

The inactivation of glycolate oxidase activity means a complete loss of activity of the enzyme. Furthermore, the decrease in glycolate oxidase activity means that activity of the enzyme is partly lost, preferably a half or less, more preferably one tenth or less, with respect to a glycolate oxidase activity of a wild strain (or a microorganism before the recombination). In order to inactivate or decrease activity of glycolate oxidase, there are methods such as introducing a mutation to the gene encoding the protein, or deleting or substituting the gene, or adding a medicine which specifically inactivates the protein, irradiating with ultraviolet rays or the like. Mutating, deleting and substituting the target gene can be carried out according to common methods known to a person skilled in the art. Specifically, an *Escherichia coli* MT-11023 strain can be mentioned as a microorganism in which activity of glycolate oxidase is inactivated by disrupting glcDEF gene encoding glycolate oxidase.

Since the activity of glycolate oxidase in *Escherichia coli* MT-11023 strain is inactivated by a gene disruption, it is possible to carry out the present invention using the strain. The present strain has been deposited as the deposition number FERM BP-10293 from Mar. 10, 2005 at International Patent Organism Depository Center of National Institute of Advanced Industrial Science and Technology at Tsukuba Central 6, 1-1-1 Higashi, Tsukuba, Ibaraki, Japan, based on the Budapest Treaty on the International Recognition of the Deposit of Microorganisms for the Purposes of Patent Procedure.

In the present invention, the term "in the form of plasmid" when introducing a gene encoding a certain target enzyme into a microorganism refers to a case where a recombinant plasmid is prepared by ligating the gene to a vector and the prepared plasmid is introduced into the microorganism by transformation or the like. Also, when a purposed gene is functionally ligated to a strong promoter constitutively functioning in a microorganism, it is possible to achieve the object of the present invention by using a plasmid in which the number of copies per microorganism cell is generally known to be small due to a property of replicon in a plasmid. As the plasmid having such a replicon, pACYC184 (GenBank accession number: X06403) and the like can be exemplified.

When carrying out the production method of the present embodiment, the required amount of microorganism microbial cell is obtained usually by culturing and growing a microorganism using a culture medium.

In the present invention, the culture medium to be used for the culture is not particularly limited as long as it contains carbon source, nitrogen source, inorganic ion and optionally traces of other organic components. As the carbon source, saccharides such as glucose, fructose, molasses and the like; organic acids such as fumaric acid, citric acid, succinic acid and the like; and alcohols such as methanol, ethanol, glycerol and others are properly used. As nitrogen source, inorganic and organic nitrogen sources such as organic ammonium salts, inorganic ammonium salts, ammonia gas, ammonia water, protein hydrolysates and others are properly used. As inorganic ion, magnesium ion, phosphate ion, potassium ion, iron ion, manganese ion, sulfate ion and others are properly used as required. As traces of organic components, vitamin, amino acid and the like and yeast extract containing vitamin, amino acid and the like, peptone, corn steep liquor, casein hydrolysate and others are properly used.

As the culture medium to be used for the culture, preferred is a liquid culture medium considering that a microorganism is provided for the industrial production.

Further, a composition of the culture medium is preferable to be polypeptone of from 0.5 g/L to 10 g/L, $Fe_2SO_4$ of from 0.02 g/L to 0.3 g/L, $K_2HPO_4$ of from 0.5 g/L to 5 g/L, $KH_2PO_4$ of from 0.5 g/L to 5 g/L, $MgSO_4.7H_2O$ of from 0.5 g/L to 5 g/L, $(NH_4)_2SO_4$ of from 0.3 g/L to 15 g/L, nicotinic acid of from 0.02 g/L to 1 g/L (a solvent is water).

When the microorganisms related to the present embodiment are cultured, the culture condition is not particularly limited, and the culture is carried out while appropriately controlling pH and temperature. Aerobic condition or anaerobic condition may be used, but preferably aerobic condition may be used. Aeration rate is preferably from 0.2 L/min to 3 L/min per the culture medium of 1 L, and more preferably from 0.5 L/min to 2 L/min. Further, stirring speed is preferably from 200 rpm to 1000 rpm and more preferably from 500 rpm to 800 rpm. By doing as described above, there can be obtained a microbial cell to give a large amount of hydroxycarboxylic acid production per weight of the microbial cells. Further, the culture may be carried out by using a gas-bubble column or the like which can guarantee a supply of dissolved oxygen corresponding to the above conditions of the aeration rate and stirring speed.

Preferred is pH of from 5 to 8, more preferred is pH of from 7.0 to 7.4, and most preferred is pH of 7.2. By doing this, there can be obtained a microbial cell that produces a large amount of hydroxycarboxylic acid per weight of the microbial cells.

Further, the temperature is preferably from 25° C. to 40° C., more preferably from 33° C. to 37° C., and most preferably 35° C. By doing this, there can be obtained a microbial cell that produces a large amount of hydroxycarboxylic acid per weight of the microbial cells.

The time required for the culture is from 12 hours to 50 hours. By doing this, there can be obtained a microbial cell that produces a large amount of hydroxycarboxylic acid per weight of the microbial cells.

As a solvent used in the production of hydroxy carboxylic acids, there may be exemplified buffer solutions such as potassium phosphate buffer solution, the aforementioned culture medium used for the culture of a microorganism, and pure water. Further, the reaction may be carried out by contacting microorganism microbial cells obtained from the previous culture to a mixture liquid of aliphatic polyhydric alcohol of the raw material and a solvent. For the microorganism microbial cells, there may be exemplified a method of using the culture broth itself after the culture is finished or a method of using only the microbial cells recovered from the culture broth.

Upon the reaction in the production method of the present invention, the reaction condition is not particularly limited and the reaction is carried out while appropriately controlling pH and temperature. For example, preferably pH is from 6 to 9, more preferably from 7.0 to 8.0, and most preferably 7.2. By doing this, there can be obtained an effect of increasing a production amount of hydroxycarboxylic acid per an amount of the microbial cells added to the reaction solution.

Further, the temperature is preferably in a range from 20° C. to 45° C., more preferably from 30° C. to 40° C., and most preferably 35° C. By doing this, there can be obtained an effect of increasing a production amount of hydroxycarboxylic acid per an amount of the microbial cells added to the reaction solution.

The reaction may be also preferably carried out in an aerobic condition. Aeration rate is preferably from 0.1 L/min to 2.0 L/min per 1 L of the reaction solution, and more preferably from 0.2 L/min to 1.0 L/min. Further, stirring speed is preferably from 200 rpm to 1000 rpm and more preferably from 400 rpm to 800 rpm. By doing this, there can be obtained an effect of increasing a production amount of hydroxycarboxylic acid per an amount of the microbial cell added to the reaction solution. Further, the reaction may be carried out by using a gas-bubble column or the like which can guarantee a supply of dissolved oxygen corresponding to the aeration rate and stirring speed conditions described above.

In addition, the reaction time is set to be from 12 hours to 96 hours so that a hydroxycarboxylic acid can be obtained with 80% or more yield rate.

A process for recovering a hydroxycarboxylic acid accumulated in the obtained reaction solution as described above is not particularly limited. However there can be adopted, for example, a process which includes removing the microbial cells from the reaction solution by centrifugation or the like and then using a synthetic adsorbent resin, a process using a precipitant, a process for separating a hydroxycarboxylic acid according to other usual collection and separation methods.

EXAMPLES

Production Example 1

Construction of *Escherichia coli* MG1655glcDEF-Deleted Strain

The entire base sequence of the genome DNA of *Escherichia coli* strain has been already reported (GenBank accession number U00096), and the base sequence of a gene (may be referred to as glcDEF hereinbelow) of glycolate oxidase of *Escherichia coli* has been also already reported (GenBank accession number L43490).

Oligonucleotides represented by Sequence No.1 (TTGGTACCGTTCTGCCAGCAACTGACG) and Sequence No.2 (TGTCTAGACTACCTCTGTGCGTCACTGG), and Sequence No.3 (GCTCTAGACGCTTTGTTGTGTTGTGTGG) and Sequence No.4 (AACTGCAGGATCGGTCAATGATTGCAGC), constructed on the basis of the gene information of the domain near glcDEF of the genome DNA of the *Escherichia coli* MG1655 strain, were used for a PCR amplification. The obtained DNA fragment was digested with restriction enzymes KpnI and XbaI, and XbaI and PstI, respectively, to obtain fragments of about 670 bp and 790 bp, respectively. These DNA fragments were mixed with a fragment obtained by digesting a temperature-sensitive cloning vector pTH18cs1 (GenBank accession number AB019610) (Hashimoto-Gotoh, T., Gene, 241, 185-191 (2000)) with KpnI and PstI, ligated using a ligase, and then transformed into an *Escherichia coli* DH5α strain (produced by Toyobo Co., Ltd.) at 30° C., to obtain a transformant which grows on an LB agar plate containing 10 μg/mL of chloramphenicol. The obtained colony was cultured in an LB liquid culture medium containing 10 μg/mL of chloramphenicol at 30° C. overnight, and a plasmid was recovered from the obtained microbial cells.

This plasmid was transformed into an *Escherichia coli* MG1655 strain at 30° C., and cultured on an LB agar plate containing 10 μg/mL of chloramphenicol at 30° C. overnight, to obtain a transformant. The obtained transformant was inoculated in an LB liquid culture medium containing 10 μg/mL of chloramphenicol and cultured at 30° C. overnight. Next, in order to obtain the cultured microbial cells thereof, the cultured transformant was applied on an LB agar plate containing 10 μg/mL of chloramphenicol to obtain colonies growing at 42° C. The obtained colonies were cultured in an LB liquid culture medium not containing medicines at 30° C. overnight, and again applied on an LB agar plate not containing medicines to obtain colonies growing at 42° C.

From the grown colonies, 100 colonies were picked up randomly, and each of them was grown on an LB agar plate without containing an antibiotic and an LB agar plate containing 10 μg/mL of chloramphenicol, to select chloramphenicol-sensitive clones growing only on the LB agar plate without containing an antibiotic. Furthermore, a fragment of about 3.8 kbp containing glcDEF was amplified by PCR using the chromosome DNA of these desired clones, to select a strain in which the glcDEF domain was deleted, and the obtained strain was named as a MG1655glcDEF-deleted strain (hereinafter may be simply referred to as ΔglcDEF). Also, the *Escherichia coli* MG1655 can be obtained from American Type Culture Collection.

Production Example 2

Construction of Lactaldehyde Reductase and Lactaldehyde Dehydrogenase Double-Expression Vector The base sequence of a gene (hereinafter, may be abbreviated as fucO) of lactaldehyde reductase of *Escherichia coli* has been already reported (GenBank accession number: M31059). Further, the base sequence of a gene (hereinafter, may be abbreviated as aldA) of lactaldehyde dehydrogenase of *Escherichia coli* has been also already reported (GenBank accession number M64541).

In order to acquire fucO, oligonucleotides represented by Sequence No.5 (GCTCTAGACGGAGAAAGTCTTATGATGGCTAACAGAATGATCCTG) and Sequence No.6 (GTGAAGCTTGCATTTACCAGGCGGTATGG) were used for a PCR amplification using the genome DNA of *Escherichia coli* MG1655 strain as a template, and the obtained DNA fragment was digested with restriction enzymes XbaI and HindIII to give a fucO fragment of about 1.2 kbp. Further, in order to acquire aldA, oligonucleotides represented by Sequence No.7 (CGAATTCCGGAGAAAGTCTTATGTCAGTACCCGTTCAACATCC) and Sequence No.8 (GCTCTAGACTCTTTCACTCATTAAGACTG) were used for a PCR amplification using the genome DNA of *Escherichia coli* MG1655 strain as a template, and the obtained DNA fragment was digested with restriction enzymes EcoRI and XbaI to give a aldA fragment of about 1.5 kbp.

Furthermore, in order to acquire a glyceraldehyde 3-phosphate dehydrogenase (GAPDH) promoter, oligonucleotides represented by Sequence No.9 (AACGAATTCTCGCAATGATTGACACGATTC) and Sequence No.10 (ACAGAATTCGCTATTTGTTAGTGAATAAAAGG) were used for a PCR amplification using the genome DNA of *Escherichia coli* MG1655 strain as a template, and the obtained DNA fragment was digested with a restriction enzyme EcoRI to give a DNA fragment of about 100 bp which encodes a GAPDH promoter.

The above-mentioned three DNA fragments were mixed with the fragment obtained by digesting plasmid pUC18 (produced by Toyobo Co., Ltd.) with restriction enzymes EcoRI and HindIII, ligated using a ligase, and then transformed into an *Escherichia coli* DH5α strain (produced by Toyobo Co., Ltd.), to obtain a transformant growing on an LB agar plate containing 50 μg/mL of ampicillin. The obtained colony was cultured in an LB liquid culture medium containing 50 μg/mL of ampicillin at 37° C. overnight. A plasmid was recovered from thus obtained microbial cells and this plasmid was named as pGAPfucO-aldA.

Production Example 3

Construction of ΔglcDEF Strain Transformant by Lactaldehyde Reductase and Lactaldehyde Dehydrogenase Double-Expression Vector The plasmid pGAPfucO-aldA obtained in Production Example 2 was transformed into the ΔglcDEF strain obtained in Production Example 1, and cultured on an LB agar plate containing 50 μg/mL of ampicillin at 37° C. overnight, to obtain ΔglcDEF/pGAPfucO-aldA strain.

Example 1

Construction of Lactaldehyde Reductase, Lactaldehyde Dehydrogenase and NADH Dehydrogenase Triple-Expression Vector, and Construction of ΔglcDEF Strain Transformant by the Vector The base sequence of a gene (hereinafter, may be abbreviated as ndh) of NADH dehydrogenase of *Escherichia coli* has been already reported (GenBank accession number V00306). In order to acquire ndh, oligonucleotides represented by Sequence No.11 (CGAATTCCGGAGAAAGTCTTATGACTACGGCATTGAAAAAGATTGTG) and Sequence No.12 (GGTCTAGACGATTAATGCAACTTCAAACG) were used for a PCR amplification using the genome DNA of *Escherichia coli* MG1655 strain as a template, to obtain a ndh fragment of about 1.3 kbp. The obtained ndh fragment was treated with T4 DNA polynucleotide kinase.

This DNA fragment was mixed with a fragment obtained by that the pGAPfucO-aldA plasmid constructed in Production Example 2 was digested with HindIII and then subjected to a blunt-end treatment and a dephosphorylation treatment, ligated using a ligase, and transformed into *Escherichia coli* DH5α strain (produced by Toyobo Co., Ltd.), to obtain a transformant growing on an LB agar plate containing 50 μg/mL of ampicillin. The obtained colonies were cultured in an LB liquid culture medium containing 50 μg/mL of ampicillin at 37° C. overnight, and a plasmid was recovered from the obtained microbial cells, and the obtained plasmid was named as pGAPfucO-aldA-ndh. The obtained plasmid pGAPfucO-aldA-ndh was transformed into the ΔglcDEF strain obtained in Production Example 1 and cultured on an LB agar plate containing 50 μg/mL of ampicillin at 37° C. overnight, to obtain the ΔglcDEF/pGAPfucO-aldA-ndh strain.

Example 2

Production of Glycolic Acid by ΔglcDEF/pGAPfucO-aldA-ndh Strain

The ΔglcDEF/pGAPfucO-aldA strain obtained in Example 1 was inoculated in 25 mL of LB Broth, Miller's culture broth (Difco244620) as a culture medium contained in a conical flask, and cultured overnight with stirring at 120 rpm at a culture temperature of 35° C., as preculture. Then, the whole amount of the preculture broth was transferred to a 1 L-fermentor (BMJ-01, culture apparatus manufactured by ABLE Corporation) containing 475 g of the culture medium of the composition shown below to carry out culture. The culture was carried out under the conditions of atmospheric pressure, an aeration rate of 0.5 L/min, a stirring speed of 800 rpm, a culture temperature of 35° C. and pH7.2 (adjusted with an aqueous $NH_3$ solution). After the initial glucose was completely exhausted under the above conditions, glucose of 40 g in total was supplied at a variable rate to give less than 0.1 g/L of glucose concentration in the culture medium for the remaining time.

<The Culture Medium Composition>
Polypetone: 7 g/L
Glucose: 30 g/L
Nicotinic acid: 0.1 g/L
$Fe_2SO_4$: 0.09 g/L
$K_2HPO_4$: 2 g/L
$KH_2PO_4$: 2 g/L
$MgSO_4.7H_2O$: 2 g/L
$(NH_4)_2SO_4$: 5 g/L
Solvent: water The microbial cells at 24 hours after the start of culturing were collected by centrifugation (8,000 rpm for 20 minutes). The wet microbial cells of 4.5 g after the collection of microbial cells were weighed and then suspended in distilled water together with ethylene glycol of 65 g to obtain 500 mL of the final liquid amount. The suspension was transferred to a fermentor of a culture apparatus BMJ-01 manufactured by ABLE Corporation to carry out the reaction for 70 hours. The reaction was carried out under the conditions including atmospheric pressure, an aeration rate of 0.25 L/min, a stirring speed of 550 rpm, a culture temperature of 35° C. and pH 7.2 (adjusted with an aqueous $NH_3$ solution). The amount of glycolic acid accumulated in the obtained reaction solution was quantified by using high speed liquid chromatography produced by Hitachi, Ltd. under the conditions described below.

Column: ULTRON PS-80H (produced by Shinwa Chemical Industries Ltd.)
Eluted solution: perchloric acid aqueous solution (pH2.1)
Flow rate: 1.0 mL/min
Detector: UV detector
Wavelength for measurement: 280 nm Further, the dry microbial cell weight of the microbial cells used in the reaction was obtained from the dry weight after drying a part of wet microbial cells at 50° C. With the ΔglcDEF/pGAPfucO-aldA-ndh strain, 39.8 g of glycolic acid was produced per 1 g of the dry microbial cells.

Further, the growth rate of the ΔglcDEF/pGAPfucO-aldA-ndh strain was the same as that of the ΔglcDEF/pGAPfucO-aldA strain in Comparative Example 1, and it was confirmed that the growth delay by enhancing nad gene did not occur.

Comparative Example 1

Production of Glycolic Acid by ΔglcDEF/pGAPfucO-aldA Strain

For the ΔglcDEF/pGAPfucO-aldA strain obtained in Production Example 3, the culture and the production of glycolic acid were carried out in the same manner as in Example 2. The amount of produced glycolic acid was 20.2 g per 1 g of the dry microbial cells of the ΔglcDEF/pGAPfucO-ald strain.

Reference Example 1

Measurement of Intracellular Content of Nicotinamide Adenine Dinucleotide in ΔglcDEF/pGAPfucO-aldA-ndh Strain and ΔglcDEF/pGAPfucO-aldA Strain For the ΔglcDEF/pGAPfucO-aldA-ndh strain and ΔglcDEF/pGAPfucO-aldA strain, the culture and the production of glycolic acid were carried out in the same manner as in Example 2.

For each of the ΔglcDEF/pGAPfucO-aldA-ndh strain and ΔglcDEF/pGAPfucO-aldA strain upon producing glycolic acid, sampling of 1 mL was carried out at a certain interval and placed into two microcentrifuge tubes and centrifuged at 4° C. to collect the microbial cells. Using one of the two microcentrifuge tubes for an NAD measurement and the other for an NADH measurement, the treatment described below was respectively carried out.

The sample for an NAD measurement was suspended by adding 400 μL of 0.04 mol/L hydrochloric acid aqueous solution per 1.5 mg of the collected wet microbial cells. The suspension was heated at 90° C. for 3 minutes, and then rapidly cooled in an ice bath. Using the supernatant of this treated liquid, the reaction solution of the composition as described below was prepared. Here, 1 mol/L Tris-HCl of pH9.0 was used. Further, as an alcoholdehydrogenase, alcoholdehydrogenase (A3263) produced by Sigma Chemical Co. was used by dissolving it with 10 mmol/L of Tris-HCl (pH 8.8) to make 400 units/mL (provided that 1 unit is an enzyme amount required for transforming 1 μmol of ethanol to acetaldehyde under the conditions of pH 8.8 and 25° C. for 1 minute). Absorption at 450 nm of the reaction solution was measured according to the protocol of Tetra Color ONE (produced by SEIKAGAKU CORPORATION). In addition, an NAD solution produced by Sigma Chemical Company was subjected to the same treatment and measurement to obtain a calibration curve, and the NAD concentration in the sample was obtained.

The sample for an NADH measurement was suspended by adding 400 μL of 0.04 mol/L potassium hydroxide aqueous solution per 1.5 mg of the collected wet microbial cells. The suspension was heated at 90° C. for 3 minutes, and then rapidly cooled in an ice bath. Using the supernatant of this treated liquid, the reaction solution of the composition described below was prepared. Here, 1 mol/L Tris-HCl of pH8.8 was used. Further, as an alcoholdehydrogenase, alcoholdehydrogenase (A3263) produced by Sigma Chemical Co. was used by dissolving it with 10 mmol/L of Tris-HCl (pH 8.8) to make 400 units/mL (provided that 1 unit is an enzyme amount required for transforming ethanol of 1 μmol to acetaldehyde under the conditions of pH 8.8 and 25° C. for 1 minute).

Figure 1:
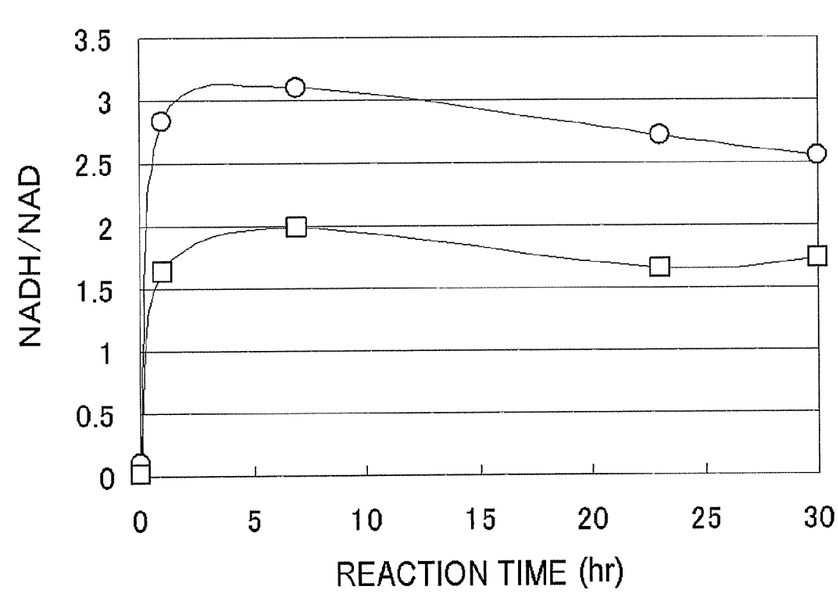
[FIG. 1] It is a graph which shows the time-course change in the NADH/NAD ratio (the NADH content/the NAD content) in the cell in Reference Example 1:
□ in the FIGURE indicates the NADH/NAD ratio of ΔglcDEF/pGAPfucO-aldA-ndh strain;
○ in the FIGURE indicates the NADH/NAD ratio of ΔglcDEF/pGAPfucO-aldA strain.

Absorption at 450 nm of the reaction solution was measured according to the protocol of Tetra Color ONE (produced by SEIKAGAKU CORPORATION). Further, an NADH solution produced by Sigma Chemical Company was subjected to the same treatment and measurement to obtain a calibration curve, and the NADH concentration in the sample was obtained. In FIG. 1, NADH/NAD ratio (NADH content/NAD content) at this time is indicated. The horizontal axis indicates the reaction time (hr) and the vertical axis indicates the NADH/NAD ratio (the NADH content/the NAD content).

It was observed that a value of the NADH/NAD ratio was always small and that NAD was regenerated from NADH in the ΔglcDEF/pGAPfucO-aldA-ndh strain.

<Composition of the Reaction Solution>
Sample supernatant: 25 μL
Tris-HCl of 1 mol/L: 25 μL
25% ethanol: 10 μL
Pure water: 20 μL
Tetra Color ONE (produced by SEIKAGAKU CORPORATION): 10 μL
Alcoholdehydrogenase: 10 μL

INDUSTRIAL APPLICABILITY

The method for producing a hydroxycarboxylic acid or the microorganism of the present invention can be used for producing hydroxycarboxylic acids such as glycolic acid useful as a raw material for polymers or an intermediate for medicines.

The invention claimed is:

1. A recombinant *Escherichia coli* which has an enhanced activity of lactaldehyde reductase from *Escherichia coli*, an enhanced activity of lactaldehyde dehydrogenase from *Escherichia coli*, and an enhanced activity of NADH dehydrogenase from *Escherichia coli*, wherein the glycolate oxidase gene is deleted, wherein the activity of NADH dehydrogenase from *Escherichia coli* is enhanced by introducing the gene of NADH dehydrogenase (ndh) of SEQ ID NO:13 into *Escherichia coli* in the form of a plasmid.

2. A method for producing a hydroxycarboxylic acid from an aliphatic polyhydric alcohol having a hydroxyl group at the end by using a recombinant *Escherichia coli* microorganism of claim 1.

3. The production method as set forth in claim 2, wherein the aliphatic polyhydric alcohol having a hydroxyl group at the end is ethylene glycol and the hydroxycarboxylic acid is glycolic acid.

* * * * *

```
SEQUENCE LISTING

<160> NUMBER OF SEQ ID NOS: 13

<210> SEQ ID NO 1
<211> LENGTH: 27
<212> TYPE: DNA
<213> ORGANISM: Artificial Sequence
<220> FEATURE:
<223> OTHER INFORMATION: Primer for PCR

<400> SEQUENCE: 1
ttggtaccgt tctgccagca actgacg                                           27

<210> SEQ ID NO 2
<211> LENGTH: 28
<212> TYPE: DNA
<213> ORGANISM: Artificial Sequence
<220> FEATURE:
<223> OTHER INFORMATION: Primer for PCR

<400> SEQUENCE: 2
tgtctagagt acctctgtgc gtcactgg                                          28

<210> SEQ ID NO 3
<211> LENGTH: 28
<212> TYPE: DNA
<213> ORGANISM: Artificial Sequence
<220> FEATURE:
<223> OTHER INFORMATION: Primer for PCR

<400> SEQUENCE: 3
gctctagacg ctttgttgtg ttgtgtgg                                          28

<210> SEQ ID NO 4
<211> LENGTH: 28
<212> TYPE: DNA
<213> ORGANISM: Artificial Sequence
<220> FEATURE:
<223> OTHER INFORMATION: Primer for PCR

<400> SEQUENCE: 4
aactgcagga tcggtcaatg attgcagc                                          28

<210> SEQ ID NO 5
<211> LENGTH: 45
<212> TYPE: DNA
<213> ORGANISM: Artificial Sequence
<220> FEATURE:
<223> OTHER INFORMATION: Primer for PCR
```

<400> SEQUENCE: 5
gctctagacg gagaaagtct tatgatggct aacagaatga ttctg    45

<210> SEQ ID NO 6
<211> LENGTH: 29
<212> TYPE: DNA
<213> ORGANISM: Artificial Sequence
<220> FEATURE:
<223> OTHER INFORMATION: Primer for PCR

<400> SEQUENCE: 6
gtgaagcttg catttaccag gcggtatgg    29

<210> SEQ ID NO 7
<211> LENGTH: 43
<212> TYPE: DNA
<213> ORGANISM: Artificial Sequence
<220> FEATURE:
<223> OTHER INFORMATION: Primer for PCR

<400> SEQUENCE: 7
cgaattccgg agaaagtctt atgtcagtac ccgttcaaca tcc    43

<210> SEQ ID NO 8
<211> LENGTH: 29
<212> TYPE: DNA
<213> ORGANISM: Artificial Sequence
<220> FEATURE:
<223> OTHER INFORMATION: Primer for PCR

<400> SEQUENCE: 8
gctctagact ctttcactca ttaagactg    29

<210> SEQ ID NO 9
<211> LENGTH: 30
<212> TYPE: DNA
<213> ORGANISM: Artificial Sequence
<220> FEATURE:
<223> OTHER INFORMATION: Primer for PCR

<400> SEQUENCE: 9
aacgaattct cgcaatgatt gacacgattc    30

<210> SEQ ID NO 10
<211> LENGTH: 32
<212> TYPE: DNA
<213> ORGANISM: Artificial Sequence
<220> FEATURE:
<223> OTHER INFORMATION: Primer for PCR

<400> SEQUENCE: 10
acagaattcg ctatttgtta gtgaataaaa gg    32

<210> SEQ ID NO 11
<211> LENGTH: 47
<212> TYPE: DNA
<213> ORGANISM: Artificial Sequence
<220> FEATURE:
<223> OTHER INFORMATION: Primer for PCR

<400> SEQUENCE: 11
cgaattccgg agaaagtctt atgactacgg cattgaaaaa gattgtg    47

<210> SEQ ID NO 12
<211> LENGTH: 29
<212> TYPE: DNA
<213> ORGANISM: Artificial Sequence
<220> FEATURE:
<223> OTHER INFORMATION: Primer for PCR

<400> SEQUENCE: 12
ggtctagacg attaatgcaa cttcaaacg                                    29

<210> SEQ ID NO 13
<211> LENGTH: 2608
<212> TYPE: DNA
<213> ORGANISM: Escherichia coli

<400> SEQUENCE: 13
ttgactacgc cattgaaaaa gattgtgatt gtcggcggcg gtgctggtgg gctggaaatg      60
gcaacacagc tggggcataa gctgggacgc aagaaaaaag ccaaaattac gctggtcgat     120
cgtaaccaca gccacctgtg gaaaccgctg ctgcacgaag tggcgactgg ctcgcttgat     180
gaaggcgtcg atgcgttgag ctatctggcc catgcgcgca atcatggttt ccagttccag     240
ctgggttccg tcattgatat tgatcgtgaa gcgaaaacaa tcactattgc agaactgcgc     300
gacgagaaag gtgaactgct ggttccggaa cgtaaaatcg cctatgacac cctggtaatg     360
gcgctgggta gcacctctaa cgatttcaat acgccaggtg tcaaagagaa ctgcattttc     420
ctcgataacc cgcaccaggc gcgtcgcttc caccaggaga tgctgaattt gttcctgaaa     480
tactccgcca acctgggcgc gaatggcaaa gtgaacattg cgattgtcgg cggcggcgcg     540
acgggtgtag aactctccgc tgaattgcac aacgcggtca gcaactgca cagctacggt     600 tacaaaggcc tgaccaacga agccctgaac gtaacgctgg tagaagcggg agaacgtatt     660
ttgcctgcgt taccgccacg tatctctgct gcggcccaca acgagctaac gaaacttggc     720
gttcgcgtgc tgacgcaaac catggtcacc agtgctgatg aaggcggcct gcacactaaa     780
gatggcgaat atattgaggc tgatctgatg gtatgggcag ccgggatcaa agcgccagac     840
ttcctgaaag atatcggtgg tcttgaaact aaccgtatca accagctggt ggtgaaccg      900 acgctgcaaa ccacccgcga tccagacatt tacgctattg gcgactgcgc gtcatgcccg     960
cgtccggaag ggggctttgt tccgccgcgt gctcaggctg caccagat ggcgacttgc      1020 gcaatgaaca acattctggc gcagatgaac ggtaagccgc tgaaaaatta tcagtataaa     1080
gatcatggtt cgctggtatc gctgtcgaac ttctccaccg tcggtagcct gatgggtaac     1140
ctgacgcgcg gctcaatgat gattgaagga cgaattgcgc gctttgtata tatctcgcta     1200
taccgaatgc atcagattgc gctgcatggt tactttaaaa ccggattaat gatgctggtg     1260
gggagtatta accgcgttat ccgtccgcgt ttgaagttgc attattgact acgccattga     1320
aaaagattgt gattgtcggc ggcggtgctg gtgggctgga atggcaaca cagctggggc     1380 ataagctggg acgcaagaaa aaagccaaaa ttacgctggt cgatcgtaac cacagccacc     1440
tgtggaaacc gctgctgcac gaagtggcga ctggctcgct tgatgaaggc gtcgatgcgt     1500
tgagctatct ggcccatgcg cgcaatcatg gtttccagtt ccagctgggt tccgtcattg     1560
atattgatcg tgaagcgaaa acaatcacta ttgcagaact gcgcgacgag aaaggtgaac     1620
tgctggttcc ggaacgtaaa atcgcctatg acaccctggt aatggcgctg gtagcacct     1680 ctaacgattt caatacgcca ggtgtcaaag agaactgcat tttcctcgat aacccgcacc     1740
aggcgcgtcg cttccaccag gagatgctga atttgttcct gaaatactcc gccaacctgg     1800
gcgcgaatgg caaagtgaac attgcgattg tcggcggcgg cgcgacgggt gtagaactct     1860

```
                                                         -continued
ccgctgaatt gcacaacgcg gtcaagcaac tgcacagcta cggttacaaa ggcctgacca    1920
acgaagccct gaacgtaacg ctggtagaag cgggagaacg tattttgcct gcgttaccgc    1980
cacgtatctc tgctgcggcc cacaacgagc taacgaaact tggcgttcgc gtgctgacgc    2040
aaaccatggt caccagtgct gatgaaggcg gcctgcacac taaagatggc gaatatattg    2100
aggctgatct gatggtatgg gcagccggga tcaaagcgcc agacttcctg aaagatatcg    2160
gtggtcttga aactaaccgt atcaaccagc tggtggtgga accgacgctg caaaccaccc    2220
gcgatccaga catttacgct attggcgact gcgcgtcatg cccgcgtccg gaaggggggct   2280 ttgttccgcc gcgtgctcag gctgcacacc agatggcgac ttgcgcaatg aacaacattc    2340
tggcgcagat gaacggtaag ccgctgaaaa attatcagta taaagatcat ggttcgctgg    2400
tatcgctgtc gaacttctcc accgtcggta gcctgatggg taacctgacg cgcggctcaa    2460
tgatgattga aggacgaatt gcgcgctttg tatatatctc gctataccga atgcatcaga    2520
ttgcgctgca tggttacttt aaaaccggat taatgatgct ggtggggagt attaaccgcg    2580
ttatccgtcc gcgtttgaag ttgcatta                                      2608
```